US00PP14594P29

(12) United States Plant Patent
Bradford

(10) Patent No.: US PP14,594 P2
(45) Date of Patent: Mar. 9, 2004

(54) NECTARINE TREE NAMED 'ROYAL BRIGHT'

(50) Latin Name: *Prunus persica*
Varietal Denomination: Royal Bright

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 116 days.

(21) Appl. No.: 10/302,977

(22) Filed: Nov. 25, 2002

(51) Int. Cl.[7] ..... A01H 5/00

(52) U.S. Cl. ..... Plt./190

(58) Field of Search ..... Plt./190

(56) References Cited

U.S. PATENT DOCUMENTS

PP7,049 P 10/1989 Bradford
PP8,947 P 10/1994 Bradford et al.

*Primary Examiner*—Anne Marie Grunberg

(57) ABSTRACT

The present invention relates to a nectarine tree, *Prunus persica*, and more particularly to a new and distinct variety broadly characterized by a large size, vigorous, hardy, self-fertile, productive and regular bearing tree. The fruit matures under the ecological conditions described in early August, with first picking on Aug. 6, 2002. The fruit is uniformly large in size, mildly acidic and sweet in flavor, globose in shape, clingstone in type, firm in texture, yellow in flesh color, and mostly red in skin color. The variety was developed as a first generation cross using 'Summer Bright' (U.S. Plant Pat. No. 7,049) yellow flesh nectarine as the selected seed parent and 'August Snow' (U.S. Plant Pat. No. 8,947) white flesh nectarine as the selected pollen parent.

1 Drawing Sheet

Botanical classification: *Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'Royal Bright'. The present variety was hybridized by me in 1993, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Summer Bright' (U.S. Plant Pat. No. 7,049) yellow flesh nectarine as the selected seed parent and 'August Snow' (U.S. Plant Pat. No. 8,947) white flesh nectarine as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected pollen parent, 'August Snow' (U.S. Plant Pat. No. 8,947) nectarine by producing nectarines that are nearly globose in shape and mature during the first week in August, but is quite distinguished therefrom by producing nectarines that are clingstone instead of freestone, yellow flesh instead of white, and acidic flavor instead of sub-acidic.

The present variety is most similar to its selected seed parent, 'Summer Bright' (U.S. Plant Pat. No. 7,049) nectarine, by producing nectarines that are nearly globose in shape, very firm in texture, clingstone in type, yellow in flesh color, and nearly full red in skin color, but is distinguished therefrom by producing fruit that is considerably larger in size and that matures about seventeen days later.

SUMMARY OF VARIETY

In summary, the present variety is characterized by a large size, vigorous, hardy, self-fertile, productive and regular bearing tree. The fruit matures under the ecological conditions described in early August, with first picking on Aug. 6, 2002. The fruit is uniformly large in size, mildly acidic and sweet in flavor, globose in shape, clingstone in type, firm in texture, yellow in flesh color, and mostly red in skin color.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 8, 2002, on the original tree during its ninth growing season. All major color code designations are by reference to the Inter-Society Color Council, National Bureau of Standards. Common color names are also used occasionally.

TREE

Size: Large, reaching a height of 12' [3.66 m.] and a spread of 10' [3.05 m.] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Large, with a maximum diameter of 5¾" [146 mm.] after the ninth growing season.

*Texture.*—Shaggy.

*Bark color.*—Grayish brown [61. gy.Br].

*Lenticels.*—Approximate Number Per Square Inch: 10. Color: Brownish orange [54. brO]. Typical Size: ⅛" to ⅜" [3.2–9.5 mm.].

Branches:

*Size.*—Diameter of limb is 2½" [64 mm.] measured 12" above the crotch, typical of *Prunus persica*, and dependent upon cultural practices and climatic conditions.

*Texture.*—Smooth on 1st year wood, increasing roughness with age.

*Color.*—1st Year Wood Topside: Strong red [12. s.R]. 1st Year Wood Underside: Brilliant yellow green [116. brill.YG]. Older Wood: Moderate brown [58. m.Br].

*Lenticels.*—Approximate Number Per Square Inch: 40. Color: Light orange yellow [70. l.OY]. Typical size: 1/16" to ⅛" [1.6–3.2 mm.].

Leaves:

*Size.*—Medium. Average Length: 5¾" [146 mm.]. Average Width: 1 11/16" [43 mm.].

*Arrangement.*—Alternate.

*Thickness.*—Medium.

*Form.*—Elliptical.

*Apex.*—Acuminate.

*Base.*—Acute, with an average base angle of 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ⅜" [9.5 mm.]. Average Thickness: 1/16" [1.6 mm.]. Color: Brilliant yellow green [116. brill.YG].

*Stipules.*—Number: 2 per leaf, up to 6 per growing tip. Average Length: 5/16" [7.9 mm.]. Color: Light yellow green [119. l.YG] becoming Dark reddish brown [44. d.rBr] with maturity.

*Glands.*—Number: 2 to 4. Position: Mostly alternate, positioned on both the petiole and base of blade. Size: Small. Form: Reniform when mature, but appear to be somewhat globose when very young. Color: Brilliant yellow green [116. brill.YG] becoming Dark reddish brown [44. d.rBr] in the centers with maturity.

*Leaf buds.*—Conic.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Strong purplish pink [247. s.pPk].

Flowers: Perfect, complete, perigynous, usually a single pistil, typically thirty or more stamens, five sepals and petal locations alternately positioned.

*Type.*—Non-showy, small.

*Average flower diameter.*—15/16" [23.8 mm.].

*Number of petals.*—Usually five.

*Petal shape.*—Oval.

*Petal margin.*—Somewhat wavy.

*Average petal diameter.*—7/16" [11.1 mm.].

*Averaqe petal length.*—9/16" [14.3 mm.].

*Petal apex.*—Rounded.

*Petal base.*—Acute.

*Petal color.*—Pale purplish pink [252. p.pPk] toward the apex smoothly blending to Strong purplish pink [247. s.pPk] toward the base.

*Anther color.*—Deep reddish orange [36. deep rO] over a Brilliant orange yellow [67. brill.OY] center.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—11/16" [17.5 mm.].

*Average stamen length.*—½" [12.7 mm.].

*Fragrance.*—Moderate when nectar is present.

*Blooming period.*—A few days later than average compared with other varieties.

*Onset of bloom.*—One percent on Mar. 4, 2002.

*Date of full bloom.*—Mar. 14, 2002.

*Duration of bloom.*—One to two weeks, dependent on ambient temperature.

*Number per cluster.*—1 to 3 with single flowers most common.

FRUIT

Maturity when described: Firm ripe, Aug. 8, 2002.

Date of first picking: Aug. 6, 2002.

Date of last picking: Aug. 14, 2002.

Size: Uniform, large.

*Average diameter axially.*—2⅞" [73.0 mm.].

*Average diameter across suture plane.*—3" [76.2 mm.].

*Typical weight.*—8.8 ounces [249 grams].

Form: Globose, slightly asymmetrical.

*Longitudinal section form.*—Circular.

*Transverse section through diameter.*—Circular.

Suture: A sharp groove from the stem to the shoulder, a shallow rounded trough along the side, a deep groove toward the apex ending about ½" [12.7 mm.] beyond the pistil point.

Ventral surface: Rounded, one lip protruding higher than the other along the side, lipped on both sides toward the apex.

Lips: Unequal along the side, fairly equal toward the apex.

Cavity: Flaring, elongated in the suture plane, suture showing on one side, Light yellow [86. l.Y] stem markings typical.

*Depth.*—¾" [19.1 mm.].

*Breadth.*—1⅛" [27.0 mm.].

Base: Truncate.
Apex: Rounded, cuneate when viewed along the suture.
Pistil point: Apical, short, depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Slightly astringent.
*Tendency to crack.*—None observed in dry season.
*Color.*—Very deep red [14. v.deep R] variegated and streaked over a Dark reddish orange [38. d.rO] background with minor Light yellowish brown [76. l.yBr] freckling on the sides toward the apex.
Flesh:
*Color.*—Brilliant Yellow [83. brill.Y] with Deep red [13. deep R] streaking more prominent toward the stone.
*Surface of pit cavavity.*—Very deep red [14. v.deep R] fibers breaking when twisted from the stone.
*Amygdalin.*—Moderate.
*Juice.*—Abundant, rich.
*Texture.*—Very firm, crisp.
*Fibers.*—Abundant, fine.
*Ripens.*—Slightly earlier toward the apex and along the lips.
*Flavor.*—Mildly acidic and sweet, typically 14 brix.
*Aroma.*—Moderate.
*Eating quality.*—Very good.

STONE

Type: Clingstone.
Form: Oval.
Hilum: Narrow, oblong.
Base: Straight.
Apex: Acute, with an average tip angle of 75 degrees and a length of 1/8" [3.2 mm.].
Sides: Equal.
Surface: Irregularly furrowed toward the apex and pitted toward the base.
Ridges: Jagged toward the base.
External color: Dark reddish brown [44. d.rBr].
Pit wall color when cracked: Grayish reddish brown [46. gy.rBr].
Cavity surface color: Deep brown [56. deep Br].
Average pit wall thickness: 1/4" [6.4 mm.].
Average width: 1 1/8" [27.0 mm.].
Average length: 1 5/8" [41.3 mm.].
Average breadth: 13/16" [20.6 mm.].
Tendency to split: Very slight.
Kernel:
*Form.*—Oval.
*Skin color.*—Light orange yellow [70. l.OY] when freshly removed.
*Pellicle color.*—Moderate yellowish brown [77. m.yBr].
*Vein color.*—Deep yellowish brown [75. deep yBr].
*Taste.*—Sweet.
*Viable.*—Yes.
*Average width.*—9/16" [14.3 mm.].
*Average length.*—7/8" [22.2 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shippinq quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected seed parent, 'Summer Bright' (U.S. Plant Pat. No. 7,049) nectarine, by producing nectarines that are nearly globose in shape, very firm in texture, clingstone in type, yellow in flesh color, and nearly full red in skin color, but is distinguished therefrom by producing fruit that is considerably larger in size and that matures about seventeen days later.

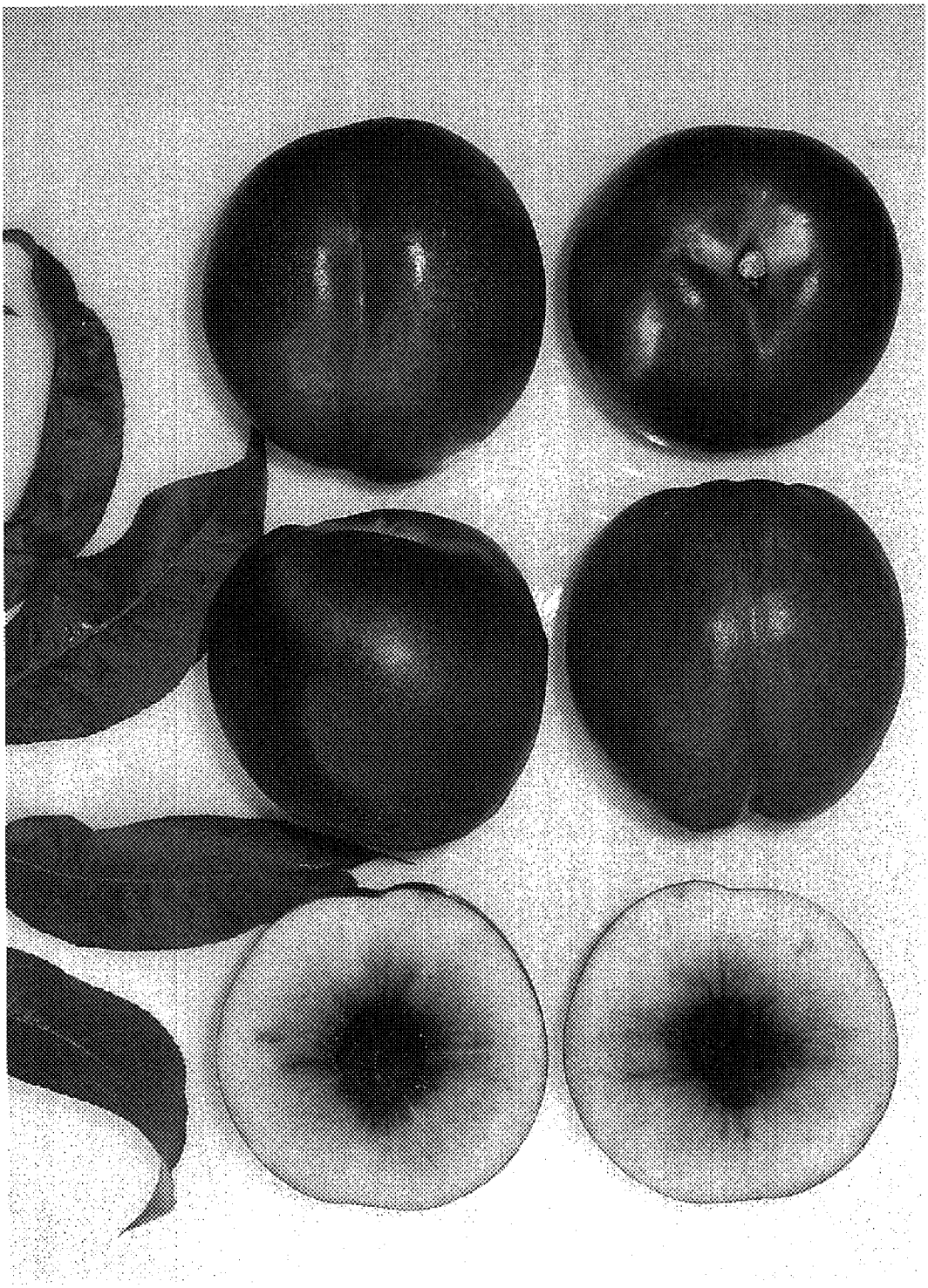

* * * * *